(12) United States Patent
Lee et al.

(10) Patent No.: US 7,811,836 B2
(45) Date of Patent: Oct. 12, 2010

(54) METHODS OF MANUFACTURING REFERENCE SAMPLE SUBSTRATES FOR ANALYZING METAL CONTAMINATION LEVELS

(75) Inventors: Jae-Seok Lee, Hwascong-si (KR); Pil-Kwon Jun, Yongin-si (KR); Sun-Hee Park, Hwaseong-si (KR); Mi-Ae Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 806 days.

(21) Appl. No.: 11/646,142

(22) Filed: Dec. 27, 2006

(65) Prior Publication Data

US 2007/0172952 A1    Jul. 26, 2007

(30) Foreign Application Priority Data

Dec. 28, 2005    (KR) .................. 10-2005-131420

(51) Int. Cl.
*H01L 21/00* (2006.01)
(52) U.S. Cl. ...................... 438/14; 438/16; 438/780; 257/E21.521
(58) Field of Classification Search ............ 438/14, 438/16, 780
See application file for complete search history.

(56) References Cited

U.S. PATENT DOCUMENTS

2006/0249713 A1* 11/2006 Peterson et al. ............. 252/500

FOREIGN PATENT DOCUMENTS

| JP | 02156636 | 6/1990 |
|----|----------|--------|
| JP | 06249764 | 9/1994 |
| JP | 11132972 | 5/1999 |
| JP | 2002184828 | 6/2002 |
| KR | 100388784 | 6/2003 |

OTHER PUBLICATIONS

English Abstract for Publication No. 02-156636.
English Abstract for Publication No. 06-249764.
English Abstract for Publication No. 11-132972.
English Abstract for Publication No. 2002-184828.
English Abstract for Publication No. 10-0388784.

* cited by examiner

*Primary Examiner*—Alexander G Ghyka
(74) *Attorney, Agent, or Firm*—F. Chau & Associates, LLC

(57) ABSTRACT

A method of manufacturing a reference sample substrate for analyzing a metal contamination level includes coating an organic silica solution including metal impurities on a semiconductor substrate and forming an oxide layer on the semiconductor substrate by thermally treating the semiconductor substrate having the coated organic silica solution. The metal impurities are substantially uniformly distributed in the oxide layer and the metal impurities are positioned at predetermined portions of the oxide layer.

19 Claims, 3 Drawing Sheets

METHODS OF MANUFACTURING REFERENCE SAMPLE SUBSTRATES FOR ANALYZING METAL CONTAMINATION LEVELS

CROSS-REFERENCE TO RELATED APPLICATIONS

This application claims priority under 35 USC §119 to Korean Patent Application No. 2005-131420, filed on Dec. 28, 2005, the contents of which are hereby incorporated by reference herein in their entirety.

BACKGROUND OF THE INVENTION

1. Technical Field

The present disclosure relates to methods of manufacturing reference sample substrates for analyzing metal contamination levels. More particularly, the present disclosure relate to methods of manufacturing reference sample substrates employed for analyzing metal contamination sources remaining on semiconductor substrates.

2. Description of the Related Art

As various contaminants may have a direct effect on the production yield of semiconductor devices, contaminants should be strictly controlled in current semiconductor manufacturing processes. Particularly, among the various contaminants, metallic contaminants may have a direct effect on the electrical reliability of a semiconductor device and thus these metallic contaminants should be more thoroughly controlled in the semiconductor manufacturing processes. For example, a metallic contamination source such as iron (Fe) and/or nickel (Ni) remaining on a semiconductor substrate is typically measured and analyzed during semiconductor manufacturing processes.

In an analysis of the metallic contamination source on a surface of the semiconductor substrate, an analysis apparatus such as a secondary ion mass spectrometry (SIMS) or a total X-ray reflection fluorescence (TXRF) is currently employed because of the minute amounts of the metal contamination source which may remain on the surface of the semiconductor substrate. When the metallic contamination source is analyzed using such an analysis apparatus, the reference sample substrate is required because the analysis of the metallic contamination source is usually performed as a quantitative analysis and a relative analysis.

The reference sample substrate is typically manufactured by at least one of the conventional methods set forth below.

For example, a reference sample substrate may be manufactured by a conventional method in which a solution including a predetermined content of metal impurities as a metal contamination source is dropped on a semiconductor substrate, and then the semiconductor wafer is dried to obtain the reference sample substrate. A reference sample substrate may also prepared by another conventional method that includes immersing a semiconductor substrate into a solution having a predetermined content of metal impurities as a metal contamination source, and drying the immersed semiconductor wafer. Additionally, the reference sample substrate may be manufactured by still another conventional method described in Japanese Patent Laid-Open Publication No. 1990-156636. In the method described in the Japanese Patent Laid-Open Publication No. 1990-156636, the reference sample substrate is manufactured by coating a soluble metallic salt as a metal contamination source remaining on a semiconductor substrate. Furthermore, Japanese Patent Laid-Open Publication No. 1994-249764 describes still another conventional method of manufacturing a reference sample substrate, which includes immersing a semiconductor substrate into an alkaline peroxide solution including a predetermined content of metal impurities as a metal contamination source, and rinsing the immersed semiconductor substrate using pure water.

When the reference sample substrate is prepared by dropping the solution having the predetermined content of the metal impurities onto the semiconductor substrate or immersing the semiconductor substrate into the solution having the predetermined content of the metal impurities, the metal contamination source may not be uniformly distributed on an entire surface of the reference sample substrate. Additionally, the metal impurities may not be uniformly distributed at desired portions of the semiconductor substrate because the semiconductor substrate has a relatively rough surface wafer and the drying process is irregularly performed about the semiconductor substrate. Thus, the total amounts of the metal impurities in reference sample substrates may differ from one another.

Moreover, when the reference sample substrate is obtained by coating the soluble metallic salt on the semiconductor substrate, the metal impurities may not be positioned at desired portions of the reference sample substrate although the metal impurities may be uniformly distributed on the reference sample substrate. Further, the total amounts of the metal impurities in the reference sample substrates may be different from one another because the compositions of the soluble metallic salts may not be readily controlled, and the semiconductor substrates may have relatively irregular surfaces.

When the reference sample substrate is manufactured by rinsing the semiconductor substrate after immersing the semiconductor wafer into the alkaline peroxide solution including the predetermined content of the metal impurities, the metal impurities may be uniformly distributed at desired portions of the reference sample substrate, and the total amounts of the metal impurities in the reference sample substrates may be substantially the same as one another. However, a thin film containing the metal impurities may still not be properly formed on the semiconductor substrate so that the thickness of the thin film containing the metal impurities on the reference sample substrate may not be varied as desired. Particularly, the reference sample substrate may not include the metal impurities with a high concentration above about $1 \times 1E13$ atoma/cm$^2$.

Furthermore, when an analysis apparatus such as the SIMS or the TXRF is employed for analyzing metal contamination levels of the conventional reference sample substrates manufactured by the above-described conventional methods, the reliability and reproductivity of data concerning the metal contamination levels may be deteriorated because the metal impurities may be irregularly distributed on the reference sample substrates and the metal impurities may not be positioned at the desired portions of the reference sample substrates. Additionally, various data relating the metal contamination levels may not be sufficiently ensured because the reference sample substrates may not have various thin films containing the metal impurities.

SUMMARY OF THE INVENTION

Example embodiments of the present invention provide methods of manufacturing reference sample substrates where metal contamination sources are uniformly distributed and the metal contamination sources are positioned at desired positions of the reference sample substrates.

In accordance with an example embodiment of the present invention, a method of manufacturing a reference sample substrate for analyzing a metal contamination level is provided. The method includes coating an organic silica solution including metal impurities on a semiconductor substrate and forming an oxide layer on the semiconductor substrate by thermally treating the semiconductor substrate having the coated organic silica solution. The metal impurities are substantially uniformly distributed in the oxide layer and the metal impurities are positioned at predetermined portions of the oxide layer.

In some example embodiments of the present invention, the metal impurities may include iron (Fe), nickel (Ni) or a mixture of iron and nickel.

In some example embodiments of the present invention, the organic silica solution may be coated on the semiconductor substrate by dropping the organic silica solution onto the semiconductor substrate, by maintaining the semiconductor substrate having the dropped organic silica solution for a predetermined time, and by rotating the semiconductor substrate having the dropped the organic silica solution. The semiconductor substrate may be maintained for about 180 seconds to about 500 seconds. Additionally, the semiconductor substrate may be revolved at a rotation speed of about 100 rotations per minute (rpm) to about 200 rpm.

In some example embodiments of the present invention, the semiconductor substrate may be thermally treated at a temperature of about 100° C. to about 800° C.

In some example embodiments of the present invention, a native oxide film may be removed from the semiconductor substrate before coating the organic silica solution. The native oxide film may be removed by immersing the semiconductor substrate into a first solution that includes an ammonia ($NH_3$) solution, a hydrogen peroxide ($H_2O_2$) solution or a mixture thereof, and by immersing the semiconductor substrate into a second solution that includes a hydrofluoric acid (HF) solution. The first solution may have a temperature of about 50° C. to about 100° C. The second solution may include about 0.5 to about 1.5 percent by weight of a diluted hydrofluoric acid (HF) solution.

In some example embodiments of the present invention, a pure oxide layer without metal impurities may be formed on the semiconductor substrate after removing the native oxide film. The pure oxide layer may be formed by immersing the semiconductor substrate into a third solution that includes a hydrochloric acid (HCl) solution and a hydrogen peroxide ($H_2O_2$) solution. The third solution may have a temperature of about 50° C. to about 100° C.

In some example embodiments of the present invention, the organic silica solution may include polymethylsilsesquioxane (PMSQ) and an ethanol solvent. For example, the organic silica solution may include about 5.0 percent by weight to about 6.0 percent by weight of PMSQ.

Example embodiments of the present invention provide a reference sample substrate having metal impurities uniformly distributed at predetermined portions which may be readily manufactured. Additionally, the total amount of the metal impurities in the reference sample substrate may be readily controlled. Further, with the example embodiments of the present invention, the reference sample substrate may have an oxide layer which includes metal impurities and has various thicknesses. As a result, the reliability and reproducibility of measured data concerning a metal contamination level may be improved when the metal contamination level is measured using the reference sample substrate manufactured in accordance with example embodiments of the present invention.

Further, the reference sample substrate may be beneficially employed in an analysis apparatus such as a SIMS or TXRF apparatus.

In accordance with an example embodiment of the present invention, a method of manufacturing a reference sample substrate for analyzing a metal contamination level is provided. The method includes coating an organic silica solution including metal impurities on the semiconductor substrate by dropping the organic silica solution onto the semiconductor substrate, maintaining the semiconductor substrate having the dropped organic silica solution for about 250 seconds to about 350 seconds and rotating the semiconductor substrate having the dropped the organic silica solution. The method further includes forming an oxide layer on the semiconductor substrate by thermally treating the semiconductor substrate having the coated organic silica solution. The metal impurities are substantially uniformly distributed in the oxide layer and the metal impurities are positioned at predetermined portions of the oxide layer.

In accordance with another example embodiment of the present invention, a method of manufacturing a reference sample substrate for analyzing a metal contamination level is provided. The method includes coating an organic silica solution including metal impurities on a semiconductor substrate and forming an oxide layer on the semiconductor substrate by thermally treating the semiconductor substrate having the coated organic silica solution at a temperature of about 250° C. to about 350° C. The metal impurities are substantially uniformly distributed in the oxide layer and the metal impurities are positioned at predetermined portions of the oxide layer.

BRIEF DESCRIPTION OF THE DRAWINGS

Example embodiments of the present invention can be understood in more detail from the following description taken in conjunction with the accompanying drawings, in which.

DESCRIPTION OF THE EMBODIMENTS

Figure 1A:
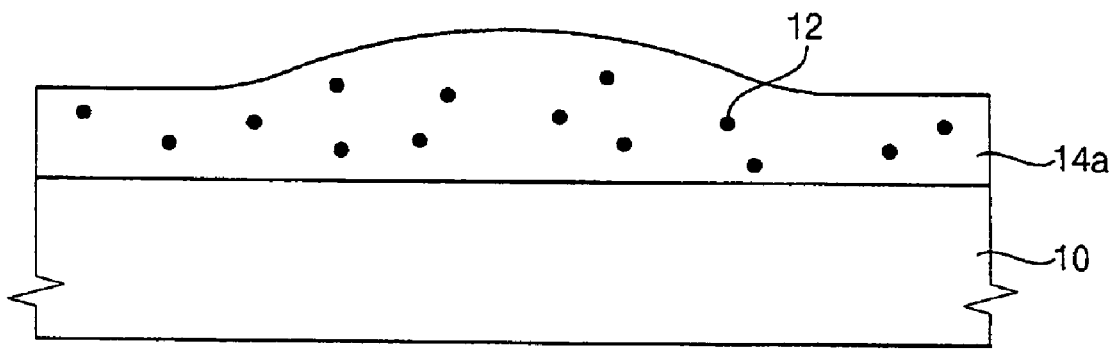
FIGS. 1A and 1B are cross-sectional views illustrating a method of manufacturing a reference sample substrate for analyzing a metal contamination level in accordance with an example embodiment of the present invention.

The present invention is described more fully hereinafter with reference to the accompanying figures, in which example embodiments of the present invention are shown. The present invention may, however, be embodied in many different forms and should not be construed as limited to the example embodiments set forth herein. In the figures, the sizes and relative sizes of layers and regions may be exaggerated for clarity.

It will be understood that when an element or layer is referred to as being "on", "connected to" or "coupled to"

another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like reference numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another elements or features as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented rotated 90 degrees or at other orientations and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-section illustrations that are schematic illustrations of idealized embodiments and intermediate structures of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Figure 1B:
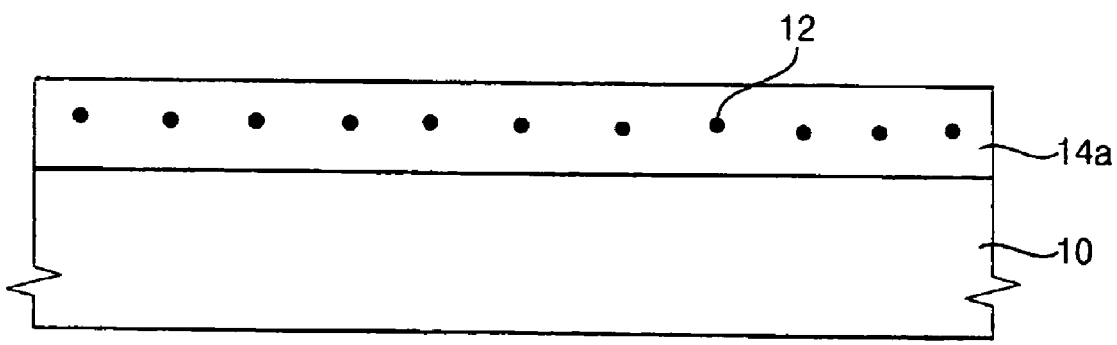

FIGS. 1A and 1B are cross-sectional views illustrating a method of manufacturing a reference sample substrate for analyzing a metal contamination level in accordance with example embodiments of the present invention.

Referring to FIG. 1A, an organic silica (silicon oxide) solution 14a including metal impurities 12 is coated on a semiconductor substrate 10. The semiconductor substrate 10 may include, for example, a silicon wafer, a silicon-on-insulator (SOI) substrate, a silicon germanium substrate, or a germanium substrate.

The metal impurities 12 may be intentionally included in the organic silica solution 14a as a metal contamination source to measure and analyze a metal contamination level of the reference sample substrate. The content of the metal impurities 12 or a concentration of the metal impurities 12 in the organic silica solution 14a may be adjusted as desired. Examples of the metal impurities 12 as the metal contamination source may include iron (Fe) and/or nickel (Ni). These metal impurities can be employed alone or in a mixture thereof.

In some example embodiments of the present invention, a process for removing a native oxide film formed on the semiconductor substrate 10 may be performed about the semiconductor substrate 10 before coating the organic silica solution 14a onto the semiconductor substrate 10. When the native oxide film includes other metal contamination sources, the desired metal contamination level of the reference sample substrate may not be properly measured and analyzed because of other metal contamination sources in the native oxide film.

In some example embodiments of the present invention, the semiconductor substrate 10 may be immersed into a first solution including, for example; an ammonia ($NH_3$) solution and/or a hydrogen peroxide ($H_2O_2$) solution. Then, the semiconductor substrate 10 may be immersed into a second solution including, for example, a hydrofluoric acid (HF) solution so as to remove the native oxide film from the semiconductor substrate 10.

The first solution may include, for example, the ammonia ($NH_3$) solution, a hydrogen peroxide ($H_2O_2$) solution or a mixture thereof. When the first solution has a temperature below about 50° C., the native oxide film may not be easily removed from the semiconductor substrate 10. When the first solution has a temperature above about 100° C., the semiconductor substrate 10 may be thermally damaged. Therefore, the first solution may have a temperature of about 50° C. to about 100° C. For example, the temperature of the first solution may be in a range of about 70° C. to about 90° C.

The second solution may include, for example, a diluted hydrofluoric acid (HF) solution. When the second solution includes below about 0.5 percent by weight of the diluted hydrofluoric acid (HF) solution based on a total weight of the second solution, the native oxide film may not be easily removed from the semiconductor substrate 10. When the second solution includes above about 1.5 percent by weight of the diluted hydrofluoric acid (HF) solution, the semiconductor substrate 10 may be damaged by the diluted hydrofluoric acid (HF) solution. Hence, the second solution may include about 0.5 percent by weight to about 1.5 percent by weight of the diluted hydrofluoric acid (HF) solution. For example, the content of the diluted hydrofluoric acid (HF) solution in the second solution may be in a range of about 0.9 percent by weight to about 1.1 percent by weight.

In some example embodiments of the present invention, a pure oxide layer without any metal impurities may be additionally formed on the semiconductor substrate 10. When the pure oxide layer is provided on the semiconductor substrate 10, defects on a surface of the semiconductor substrate 10 may be somewhat compensated. Further, the pure oxide layer may improve the adhesion strength between the semiconductor substrate 10 and the organic silica solution 14a. As the pure oxide layer does not include any metal impurities, the analysis of the metal contamination level relative to the reference sample substrate may not be affected by the pure oxide layer. In an example embodiment, the semiconductor substrate 10 may be immersed into a third solution to form the pure oxide layer on the semiconductor substrate 10. The third solution may include, for example, a hydrochloric acid (HCl) solution and/or a hydrogen peroxide ($H_2O_2$) solution.

The third solution may include, for example, the hydrochloric acid (HCl) solution, the hydrogen peroxide ($H_2O_2$) solution or a mixture thereof. When the third solution has a temperature below about 50° C., the pure oxide layer may not be properly formed on the semiconductor substrate 100. When the third solution has a temperature of above about 100° C., the semiconductor substrate 10 may be thermally damaged and the formation of the pure oxide layer may not be precisely controlled. Thus, the third solution may have a temperature of about 50° C. to about 100° C. For example, the temperature of the third solution may be in a range of about 70° C. to about 90° C.

As described above, the organic silica solution 14a including the metal impurities 12 may be coated on the semiconductor substrate 10 after removing the native oxide film from the semiconductor substrate 10. Further, the organic silica solution 14a may be coated on the semiconductor substrate 10 after forming the pure oxide layer on the semiconductor substrate 10.

In some example embodiments of the present invention, the organic silica solution 14a may include, for example, polymethylsilsesquioxane (PMSQ) and an ethanol solvent. The organic silica solution 14a may include about 5.0 percent by weight to about 6.0 percent by weight of PMSQ based on the total weight of the organic silica solution 14a. Additionally, the organic silica solution 14a may include about several to about several tens of parts per billion (ppb) of metal impurities 12 such as, for example, iron and/or nickel.

Hereinafter, a process for coating the organic silica solution 14a onto the semiconductor substrate 10 will be illustrated in detail.

The organic silica solution 14a including the metal impurities 12 may be dropped onto the semiconductor substrate 10. Then, the semiconductor substrate 10 having the dropped organic silica solution 14a may be maintained for a predetermined time so as to spread the dropped organic silica solution 14a onto the entire surface of the semiconductor substrate 10.

When the semiconductor substrate 10 having the dropped organic silica solution 14a is maintained for less than about 180 seconds, the dropped organic silica solution 14a may not be uniformly spread on the entire surface of the semiconductor substrate 10. When the semiconductor substrate 10 having the dropped organic silica solution 14a is maintained for more than about 500 seconds, the dropped organic silica solution 14a may be overflowed from an edge portion of the semiconductor substrate 10. Thus, the semiconductor substrate 10 having the dropped organic silica solution 14a may be maintained for about 180 seconds to about 500 seconds. For example, the time for maintaining the semiconductor substrate 10 having the dropped organic silica solution 14a may be in a range of about 250 seconds to about 350 seconds.

After maintaining the semiconductor substrate 10 having the dropped organic silica solution 14a for a predetermined time, the semiconductor substrate 10 having the dropped organic silica solution 14a may be revolved. Hence, the organic silica solution 14a may be more uniformly coated on the entire surface of the semiconductor substrate 10. When the semiconductor substrate 10 rotates at a rate below about 100 rotations per minute (rpm), the organic silica solution 14a may not be uniformly coated on the semiconductor substrate 10. When the semiconductor substrate 10 is revolved at a rate above about 200 rpm, the organic silica solution 14a may be bounced off from the semiconductor substrate 10. Hence, the semiconductor substrate 10 may rotate at a rate of about 100 rpm to about 200 rpm. For example, the rotation speed of the semiconductor substrate 10 may be in a range of about 130 rpm to about 170 rpm. In some example embodiments, the semiconductor substrate 10 may be rotated using a rotating apparatus such as, for example, a spin-coater.

After coating the organic silica solution 14a including the metallic impurities 12 on the semiconductor substrate 10, the semiconductor substrate 10 may be thermally treated. When a heat treatment process is performed on the semiconductor substrate 10, an oxide layer 14 including the metallic impurities 12 is formed on the semiconductor substrate 10 as shown in FIG. 1B. For example, the organic silica solution 14a coated on the semiconductor substrate 10 may be changed into the oxide layer 14 by the heat treatment process.

When the semiconductor substrate 10 is thermally treated at a temperature below about 100° C., the oxide layer 14 may not be properly formed from the organic silica solution 14a. When the heat treatment process is performed on the semiconductor substrate 10 at a temperature above about 800° C., the semiconductor substrate 10 may be thermally damaged and the oxide layer 14 may not be properly formed on the semiconductor substrate 10. Therefore, the semiconductor substrate 10 may be thermally treated at a temperature of about 100° C. to about 800° C. For example, the heat treatment process may be performed on the semiconductor substrate 10 at a temperature of about 200° C. to about 500° C. Preferably, the oxide layer 14 may be formed on the semiconductor substrate 10 at a temperature of about 250° C. to about 350° C.

As the heat treatment process may be carried out after the organic silica solution 14a is uniformly formed on the surface of the semiconductor substrate 10, the reference simple substrate may have uniformly distributed metal impurities 12 therein, and the metal impurities 12 may be properly positioned at desired positions of the reference sample substrate. That is, the uniformly distributed metal impurities 12 may have desired depths from an upper face of the reference sample substrate.

In some example embodiments of the present invention, the oxide layer 14 may have a thickness varied in accordance with an adjustment of an amount of the organic silica solution 14a on the semiconductor substrate 10.

In some example embodiments of the present invention, a nitride layer may be formed on a semiconductor substrate by processes substantially the same as the above-described process using an organic nitride solution instead of the organic silica solution.

According to example embodiments of the present invention, metal impurities may be uniformly distributed in a reference sample substrate, and the metal impurities may be positioned at desired portions of the reference sample substrate. Further, the thickness of an oxide layer including the metal impurities may be varied by adjusting an organic solution including the metal impurities. As a result, the reference sample substrate may provide a precise metal contamination level, and thereby the productivity of the reference sample substrate may be improved.

Manufacturing a Reference Sample Substrate

After a semiconductor substrate having a diameter of about 200 millimeters (mm) was prepared, a native oxide film remaining on the semiconductor substrate was removed. The native oxide film was removed using a first solution that included about 80 percent by weight of an ammonia ($NH_3$) solution and about 20 percent by weight of a hydrogen peroxide ($H_2O_2$) solution, and a second solution that included about 1 percent by weight of a hydrofluoric acid (HF) solution.

A pure oxide layer without any metal impurities was formed on the semiconductor substrate. The pure oxide layer was formed using a third solution that included about 80 percent by weight of a hydrochloric acid (HCl) solution and about 20 percent by weight of a hydrogen peroxide ($H_2O_2$) solution.

An organic silica solution including metal impurities was dropped onto a surface of the semiconductor substrate. The organic silica solution included an ethanol solvent containing about 5.5 percent by weight of PMSQ. The concentration of the metal impurities in the organic silica solution was about 10 ppb.

After the semiconductor substrate having the dropped organic silica solution was maintained for about 5 minutes, the semiconductor substrate was revolved at a rotation speed of about 150 rpm using a spin coater. Thus, the organic silica solution was uniformly distributed on the entire surface of the semiconductor substrate.

The semiconductor substrate having the uniformly distributed organic silica solution was thermally treated at a temperature of about 300° C. In a heat treatment process, undesired carbon contained in the organic silica solution was removed so that the organic silica solution was changed into an oxide layer. Therefore, a reference sample substrate having the oxide layer was obtained. As the organic silica solution included the metal impurities, the oxide layer also included the metal impurities. Additionally, the metal impurities were uniformly distributed in the oxide layer because the organic silica solution was uniformly formed on the entire surface of the semiconductor substrate. Furthermore, the metal impurities were positioned at proper positions of the oxide layer through the above-described processes. The oxide layer had a thickness of about 2,000 Å.

Measurement of a Thickness Uniformity of an Oxide layer in a Reference Sample Substrate The thickness of the oxide layer in the reference sample substrate obtained by the above-described processes was measured using a thickness measurement apparatus such as, for example, a Tox meter.

Figure 2:
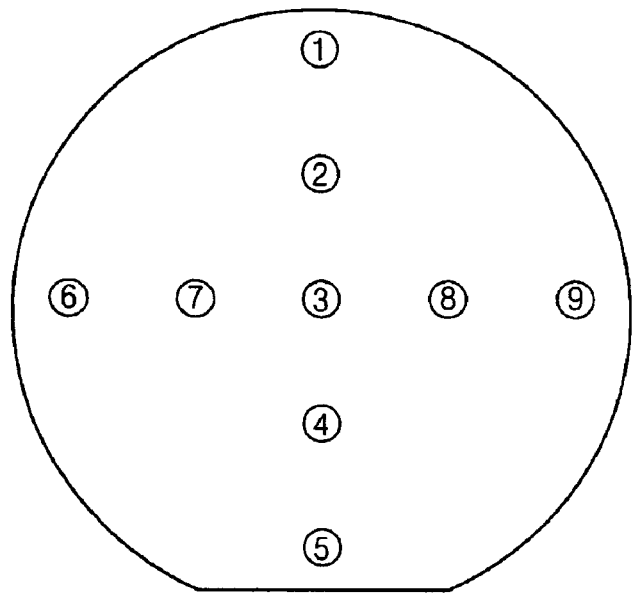
FIG. 2 is a plan view illustrating a method for measuring a thickness uniformity of an oxide layer formed on a reference sample substrate in accordance with an example embodiment of the present invention.

FIG. 2 is a plan view illustrating a method for measuring the thickness uniformity of the oxide layer formed on the reference sample substrate.

As shown in FIG. 2, the thickness uniformity of the oxide layer was measured relative to nine points of the oxide layer formed on the reference sample substrate. The measured results are shown in the following Table 1. The thickness of the nine points of the oxide layer was measured three times. The unit used for measuring the thickness of the oxide layer is angstrom (Å).

TABLE 1

| | The Number of Measurement | | | | | | | | |
|---|---|---|---|---|---|---|---|---|---|
| | 1 | 2 | 3 | 4 | 5 | 6 | 7 | 8 | 9 |
| 1 | 2027 | 1984 | 2003 | 2058 | 2107 | 2097 | 2038 | 2032 | 2048 |
| 2 | 2099 | 2088 | 2123 | 2191 | 2199 | 2064 | 2083 | 2205 | 2241 |
| 3 | 2107 | 2217 | 1868 | 2077 | 2755 | 2035 | 2085 | 2304 | 1991 |

As shown in Table 1, the thickness difference among the nine points of the oxide layer is below about 10 percent. Therefore, the oxide layer on the reference sample substrate has a considerably uniform thickness. As the oxide layer has the uniformity thickness, the metal impurities in the oxide layer are also uniformly distributed in the oxide layer and positioned at desired portions of the oxide layer.

Evaluation of an Amount of Metal Impurities Relative to a Concentration of Metal Impurities To evaluate the relationship between a concentration of the metal impurities of reference sample substrate and a total amount of the metal impurities in an organic solution employed for manufacturing the reference sample substrate, six reference sample substrates were prepared. The reference sample substrates were manufactured by processes substantially the same as the above-described processes except for the concentrations and amounts of the metal impurities contained in organic silica solutions.

A first reference sample substrate was prepared using an organic silica solution including about 1 ppb of iron, and a second reference sample substrate was obtained using an organic silica solution including about 10 ppb of iron. A third reference sample substrate was manufactured using an organic silica solution including about 100 ppb of iron, and a fourth reference sample substrate was obtained using an organic silica solution including about 1 ppb of nickel. Further, a fifth reference sample substrate was prepared using an organic silica solution including about 10 ppb of nickel, and a sixth reference sample substrate was manufactured using an organic silica solution including about 100 ppb of nickel.

The total amounts of the metal impurities in the first to the sixth reference sample substrates were measured using an inductively coupled plasma-mass spectrometer (ICP-MS).

Figure 3:
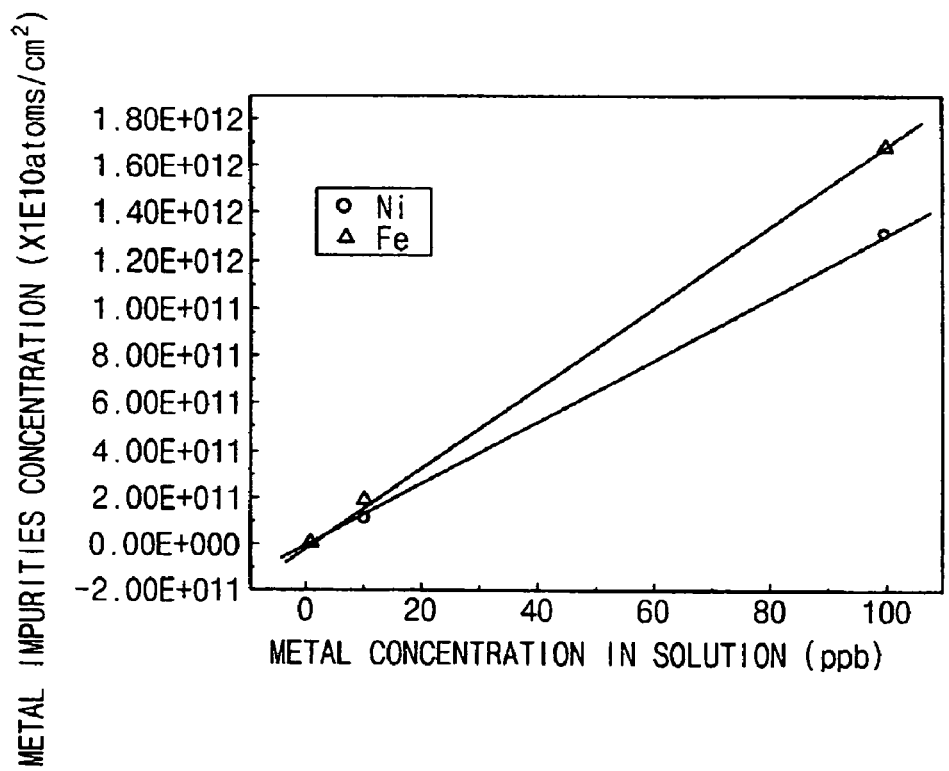
FIG. 3 is a graph illustrating relationships between the total amounts of metal impurities in reference sample substrates and concentrations of the metal impurities included in organic silica solutions in accordance with an example embodiment of the present invention.

FIG. 3 is a graph illustrating relationships between the total amounts of metal impurities in reference sample substrates and concentrations of metal impurities included in organic silica solution in accordance with example embodiments of the present invention.

As shown in FIG. 3, the total amounts of the metal impurities in the first, the second and the third reference sample substrates are in proportion to the concentrations of the metal impurities contained in the organic silicon solutions. Additionally, the total amounts of the metal impurities in the fourth, the fifth and the sixth reference sample substrates are in proportion to the concentrations of the metal impurities contained in the organic silicon solutions.

According to some example embodiments of the present invention, the concentration of metal impurities in an organic solution may be in proportion to the total amount of the metal impurities in a reference sample substrate. Therefore, the total amount of the metal impurities in the reference sample substrate may be readily controlled by, for example, adjusting the concentration of the metal impurities included in the organic solution.

Evaluation of a Distribution of Metal Impurities in a Reference Sample Substrate A reference sample substrate was prepared by processes substantially the same as the above-described processes.

Figure 4:
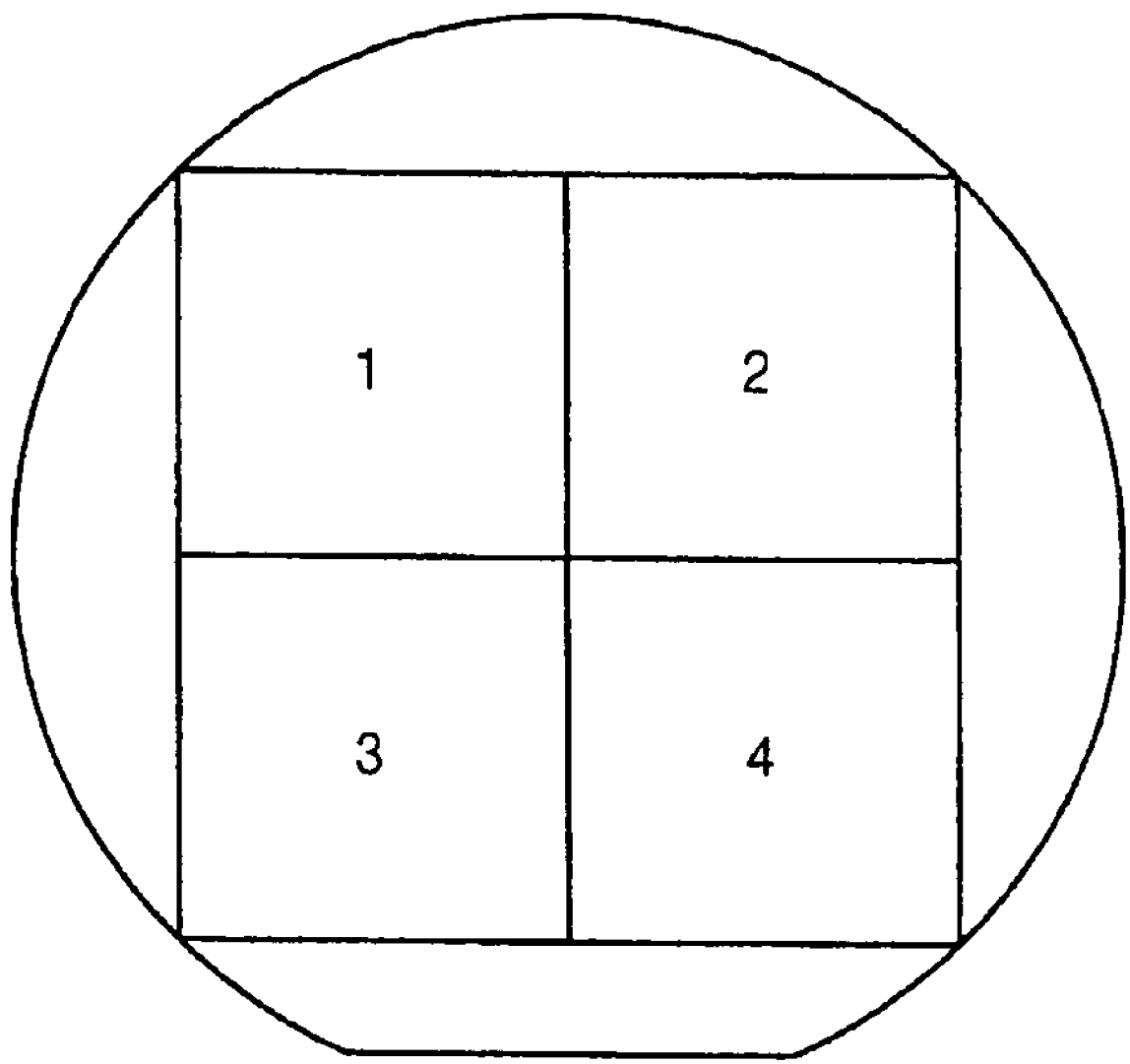
FIG. 4 is a plan view illustrating a distribution of metal impurities in a reference sample substrate in accordance with an example embodiment of the present invention.

FIG. 4 is a plan view illustrating a distribution of the metal impurities in a reference sample substrate in accordance with an example embodiment of the present invention.

As shown in FIG. 4, amounts of the metal impurities were measured as four regions of the reference sample substrate. The amounts of the metal impurities were measured by a chemical analyzing method using an ICP-MS. The measured results are shown in the following Table 2.

TABLE 2

|  | 1 | 2 | 3 | 4 |
|---|---|---|---|---|
| Concentration of Fe [$1 \times E10$ atoms/cm$^2$] | 671.56 | 633.47 | 542.89 | 615.97 |
| Concentration of Ni [$1 \times E10$ atoms/cm$^2$] | 608.43 | 549.64 | 520.82 | 559.63 |

As shown in Table 2, the amounts of the metal impurities are substantially similar relative to four regions of the reference sample substrate. Thus, the metal impurities may be uniformly distributed in the reference sample substrate according to example embodiments of the present invention.

Evaluation of Total Amount of Metal Impurities in a Reference Sample Substrate

To evaluate the total amount of metal impurities in a reference sample substrate, three reference sample substrates were prepared. These reference sample substrates were manufactured by processes substantially the same as the above-described processes. The three reference sample substrates were prepared, using organic silica solutions having concentrations of metal impurities of about 100 ppb, respectively.

The total amounts of the metal impurities in the three reference sample substrates were measured by a chemical analysis method using, for example, an ICP-MS.

When the total amounts of the metal impurities in the three reference sample substrates were measured, the difference obtained among the measured total amounts of the metal impurities was below about 5% based on each of the measured total amounts of the metal impurities in the three reference sample substrates. Accordingly, the total amount of the metal impurities in the reference sample substrate may be readily controlled, for example by adjusting a concentration control of the metal impurities.

According to example embodiments of the present invention, a reference sample substrate having metal impurities uniformly distributed at predetermined portions may be readily manufactured. Additionally, the total amount of the metal impurities in the reference sample substrate may be readily controlled. Further, the reference sample substrate may have an oxide layer including metal impurities and have various thicknesses. As a result, the reliability and reproductivity of measured data concerning the metal contamination level may be improved when the metal contamination level is measured using the reference sample substrate in accordance with example embodiments of the present invention. Further, the reference sample substrate may be beneficially employed in an analysis apparatus such as, for example, a SIMS or TXRF apparatus.

Having described the example embodiments of the present invention, it is further noted that it is readily apparent to those of reasonable skill in the art that various modifications may be made without departing from the spirit and scope of the invention which is defined by the metes and bounds of the appended claims.

What is claimed is:

1. A method of manufacturing a reference sample substrate for analyzing a metal contamination level, comprising:
    coating an organic silica solution including metal impurities on a semiconductor substrate, wherein the coating of the organic silica solution comprises:
    dropping the organic silica solution onto the semiconductor substrate;
    maintaining the semiconductor substrate having the dropped organic silica solution for a time of at least about 180 seconds; and
    rotating the semiconductor substrate having the dropped organic silica solution and wherein the semiconductor substrate having the dropped organic silica solution is maintained for the time of at least about 180 seconds prior to the rotating of the semiconductor substrate having the dropped organic silica solution; and
    forming an oxide layer on the semiconductor substrate by thermally treating the semiconductor substrate having the coated organic silica solution, wherein the metal impurities are uniformly distributed in the oxide layer and the metal impurities are positioned at predetermined portions of the oxide layer.

2. The method of claim 1, wherein the metal impurities comprise iron (Fe), nickel (Ni) or a mixture of iron and nickel.

3. The method of claim 1, wherein the semiconductor substrate is maintained for about 180 seconds to about 500 seconds.

4. The method of claim 1, wherein the semiconductor substrate is revolved at a rotation speed of about 100 rotation per minute (rpm) to about 200 rpm.

5. The method of claim 1, wherein the semiconductor substrate is thermally treated at a temperature of about 100° C. to about 800° C.

6. The method of claim 1, wherein prior to coating the organic silica solution, further comprising removing a native oxide film from the semiconductor substrate.

7. The method of claim 6, wherein the removing of the native oxide film comprises:
    immersing the semiconductor substrate into a first solution that includes an ammonia ($NH_3$) solution, a hydrogen peroxide ($H_2O_2$) solution or a mixture of the ammonia ($NH_3$) solution and the hydrogen peroxide ($H_2O_2$) solution; and
    immersing the semiconductor substrate into a second solution that includes a hydrofluoric acid (HF) solution.

8. The method of claim 7, wherein the first solution has a temperature of about 50° C. to about 100° C.

9. The method of claim 7, wherein the second solution includes about 0.5 to about 1.5 percent by weight of a diluted hydrofluoric acid (HF) solution.

10. The method of claim 6, further comprising forming a pure oxide layer without metal impurities on the semiconductor substrate after removing the native oxide film.

11. The method of claim 10, wherein the forming of the pure oxide layer comprises immersing the semiconductor substrate into a third solution that includes a hydrochloric acid (HCl) solution and a hydrogen peroxide ($H_2O_2$) solution.

12. The method of claim 11, wherein the third solution has a temperature of about 50° C. to about 100° C.

13. The method of claim 1, wherein the organic silica solution further comprises polymethylsilsesquioxane (PMSQ) and an ethanol solvent.

14. The method of claim 13, wherein the organic silica solution comprises about 5.0 percent by weight to about 6.0 percent by weight of PMSQ.

15. A method of manufacturing a reference sample substrate for analyzing a metal contamination level, comprising:
    coating an organic silica solution including metal impurities on the semiconductor substrate by dropping the organic silica solution onto the semiconductor substrate, maintaining the semiconductor substrate having the dropped organic silica solution, and rotating the semiconductor substrate having the dropped the organic silica solution, wherein the semiconductor substrate having the dropped organic silica solution is maintained for about 250 seconds to about 350 seconds prior to the rotating of the semiconductor substrate having the dropped organic silica solution; and forming an oxide layer on the semiconductor substrate by thermally treating the semiconductor substrate having the coated organic silica solution, wherein the metal impurities are uniformly distributed in the oxide layer and the metal impurities are positioned at predetermined portions of the oxide layer.

16. The method of claim 15, wherein the organic silica solution further comprises polymethylsilsesquioxane (PMSQ) and an ethanol solvent and wherein the metal impurities comprise iron (Fe), nickel (Ni) or a mixture of iron and nickel.

17. The method of claim 15, wherein the semiconductor substrate is revolved at a rotation speed of about 130 rotation per minute (rpm) to about 170 rpm.

18. The method of claim 15, wherein the semiconductor substrate is thermally treated at a temperature of about 250° C. to about 350° C.

19. A method of manufacturing a reference sample substrate for analyzing a metal contamination level, comprising:

coating an organic silica solution including metal impurities on a semiconductor substrate, wherein the coating of the organic silica solution comprises:

dropping the organic silica solution onto the semiconductor substrate;

maintaining the semiconductor substrate having the dropped organic silica solution; and rotating the semiconductor substrate having the dropped the organic silica solution at a rotation speed of about 100 rotation per minute (rpm) to about 200 rpm and wherein the semiconductor substrate having the dropped organic silica solution is maintained for about 180 seconds to about 500 seconds prior to the rotating of the semiconductor substrate having the dropped organic silica solution; and forming an oxide layer on the semiconductor substrate by thermally treating the semiconductor substrate having the coated organic silica solution at a temperature of about 250° C. to about 350° C. after the rotating of the semiconductor substrate having the dropped organic silica solution, wherein the metal impurities are uniformly distributed in the oxide layer and the metal impurities are positioned at predetermined portions of the oxide layer.

* * * * *